United States Patent [19]

Bazile et al.

[11] 4,220,793

[45] Sep. 2, 1980

[54] PROCESS FOR PREPARING A THIOPHENE DERIVATIVE

[75] Inventors: Yves Bazile; Paul de Cointet de Fillain, both of Sisteron; Charles Pigerol, Saint-Ouen, all of France

[73] Assignee: Labaz, Paris, France

[21] Appl. No.: 960,564

[22] Filed: Nov. 14, 1978

[30] Foreign Application Priority Data

Nov. 17, 1977 [FR] France ................................ 77 34554

[51] Int. Cl.$^2$ ......................................... C07D 333/44
[52] U.S. Cl. .................................................... 549/68
[58] Field of Search ................... 260/332.2 C; 549/71, 549/68

[56] References Cited

U.S. PATENT DOCUMENTS

3,733,319  5/1973  Henry et al. ......................... 260/240

FOREIGN PATENT DOCUMENTS

211959  8/1908  Fed. Rep. of Germany ........... 562/419
908023  4/1954  Fed. Rep. of Germany ........ 260/332.2

*Primary Examiner*—Robert Gerstl
*Attorney, Agent, or Firm*—Mason, Kolehmainen, Rathburn & Wyss

[57] ABSTRACT

A process for preparing 5-nitro-2-thenoic acid by oxidation of the corresponding aldehyde is described.

4 Claims, No Drawings

PROCESS FOR PREPARING A THIOPHENE DERIVATIVE

The present invention relates to a process for preparing a thiophene derivative and also to the derivative obtained by the said process.

The invention relates more particularly to a process for the preparation of 5-nitro-2-thenoic acid of the formula:

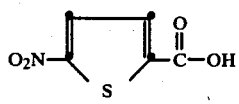

5-Nitro-2-thenoic acid is a known product having been described in Chemical Abstracts 47, 2166 G.

This product is of particular value for the preparation of compounds having pharmacological properties. For instance, 5-nitro-2-thenoic acid can be used for the preparation of antiparasitic compounds such as those described in Chimica Therapeutica 5, 270–273 (1970).

The methods described in the chemical literature regarding the preparation of 5-nitro-2-thenoic acid starting from 5-nitro-2-formyl-thiophene are essentially designed for laboratory use and their extension to the industrial scale is difficult and should even be completely avoided.

For example, a process for preparing 5-nitro-2-thenoic acid has been cited in Chemical Abstracts 47, 2166 G that consists in adding 5-nitro-2-formyl-thiophene to a mixture of nitric acid and acetic acid and subsequently treating the diacetate so formed with concentrated sulphuric acid, which provides 5-nitro-2-thenoic acid in a yield of 33%.

As indicated furtheron, a process based on the addition of this aldehyde to a reaction medium is to be absolutely prohibited on the industrial plane.

Furthermore, Bull. Soc. Chim. France, 1152, 701–702, as well as J. Am. Chem. Soc., 74, 1356–1357 (1952) describe a process for the preparation of 5-nitro-2-thenoic acid by oxidation of 5-nitro-2-formyl-thiophene with potassium permanganate.

It is quite clear that the use of potassium permanganate as an oxidating agent would be very expensive on the industrial scale.

The need for finding an industrial process for obtaining 5-nitro-2-thenoic acid is thus of paramount importance.

Up to present, the synthesis of aromatic carboxylic acids by oxidation of aromatic aldehydes by means of halogens in a basic medium has been studied very little.

As an example of such a method, mention may be made of Chemical Abstracts 50, 11503e (1956) which describes the oxidation of furfural by means of sodium hypobromite in an alkaline medium.

This process consists essentially in introducing bromine into an aqueous solution of sodium hydroxide and then adding furfural to this reaction medium maintained at 0° C. in order to obtain 2-furoic acid.

In view of the similarity as regards chemical structure between 2-furoic acid and 5-nitro-2-thenoic acid, it would appear obvious to utilize the aforesaid process starting from 5-nitro-2-formyl-thiophene. However, such a process when applied to the preparation of 5-nitro-2-thenoic acid is to be avoided on the industrial scale.

In fact, 5-nitro-2-formyl-thiophene presents a particularly high degree of toxicity creating for the operators acute problems of cutaneous allergy.

As a result of this high degree of toxicity, the handling of this aldehyde must be reduced to the minimum which consequently obviates all possibility of purification.

It is consequently essential that a process be found for preparing 5-nitro-2-thenoic acid starting from 5-nitro-2-formyl-thiophene which has the following qualities:
simplicity as regards procedure
use of crude 5-nitro-2-formyl-thiophene reducing manipulation to a maximum for instance by avoiding the need for purification and addition to a reaction medium
high yield
a production cost which is a low as possible Attempts have been made to prepare 5-nitro-2-thenoic acid by means of the method described in the aforementioned 1956 Chemical Abstracts reference after the order of introduction of the reagents had been modified so as to avoid any addition of 5-nitro-2-formyl-thiophene to the reaction medium. For this purpose, the method described in German Pat. No. 116,452 of the German Democratic Republic was taken as a basis. This method is essentially characterized by the addition of bromine to a reaction medium maintained at 10° C., the said medium being obtained from an aqueous suspension of 5-nitro-2-formyl-thiophene to which an aqueous solution of sodium hydroxide has been added. However, trials have shown that this alteration to the process described in the said Chemical Abstracts reference is quite unacceptable.

None of the desired acid could, in fact, be obtained starting, for example, from 0.1 mol of 5-nitro-2-formyl-thiophene, 0.2 mol of aqueous sodium hydroxide and 0.1 mol of bromine.

Similar results were obtained starting from 5-nitro-2-formyl-furan used under the same conditions.

On the other hand, 4-nitro-2-formyl-thiophene gave, under the same operating conditions, the corresponding acid in crude form in a yield of 45%, which represents a yield of 33% in pure acid.

It has now been discovered, in accordance with the invention, that it is nevertheless possible to obtain 5-nitro-2-thenoic acid from a halogen, an alkali metal hydroxide and 5-nitro-2-formyl-thiophene without having to introduce the aldehyde into the reaction medium.

Thus, in accordance with one aspect of the process of the invention, an aqueous solution of alkali metal hydroxide, for example sodium hydroxide, is introduced into a reaction medium formed by adding a halogen, such as chlorine, bromine or iodine, to an aqueous suspension of 5-nitro-2-thiophene, the introduction of the hydroxide being so carried out that the pH of the medium is maintained between 7 and 11 and preferably between 7 and 8 during the oxidation reaction.

For instance, an aqueous solution of sodium hydroxide will be introduced into the reaction medium maintained at a temperature between room-temperature and 40° C., the oxidation reaction itself taking place at a temperature between room-temperature and 80° C.

In this manner, 5-nitro-2-thenoic acid was obtained in a yield of 98.5% in crude product or 81% in pure product starting from 0.1 mol of 5-nitro-2-formyl-thiophene, 0.2 mol of aqueous sodium hydroxide and 0.1 mol of bromine, the pH of the reaction medium varying from 7 to 9.5 in the course of the reaction.

Furthermore, it has been discovered, in accordance with another aspect of the present invention, that it is possible to obtain pure 5-nitro-2-thenoic acid in a yield superior to 80% by introducing a halogen, such as chlorine, bromine or iodine, into an aqueous suspension of 5-nitro-2-formyl-thiophene to which an alkali metal carbonate, an alkali metal bicarbonate or an alkali metal acetate/acetic acid mixture has been previously added so that the oxidation reaction takes place at a pH between 4.5 and 11.

The alkali metal carbonate or bicarbonate will be, for instance, sodium carbonate or bicarbonate.

The halogen will be introduced into the reaction medium maintained at a temperature between room-temperature and 40° C. and the oxidation reaction itself will take place at a temperature between room-temperature and 80° C.

As an example, a trial performed with 5-nitro-2-formyl-thiophene and bromine in a medium maintained at pH=4.6 by means of a acetic acid/sodium acetate mixture provided crude 5-nitro-2-thenoic acid in a yield of 98.5% or the pure acid in a yield of 81%.

Under the same operating conditions, 4-nitro-2-formyl-thiophene only provided 10% in crude 4-nitro-2-thenoic acid while 5-nitro-2-formyl-furan only gave 5% in 5-nitro-2-furoic acid.

Likewise, in a reaction medium maintained at a pH between 11 and 8.6 by means of sodium carbonate, 98.2% of crude 5-nitro-2-thenoic acid or 81% in pure acid were obtained from 5-nitro-2-formyl-thiophene and bromine while, under the same operating conditions, 4-nitro-2-formyl-thiophene provided 4-nitro-2-thenoic acid in a yield which was practically nil.

Mention may also be made of a trial whereby, in a reaction medium maintained at a pH between 8 and 7.3 by means of sodium bicarbonate, 5-nitro-2-formyl-thiophene and bromine provided crude 5-nitro-2-thenoic acid in a yield of 98.2% which represents a yield of 81% in pure acid. On the other hand, under the same operating conditions, 4-nitro-2-formyl-thiophene gave the corresponding crude acid in a yield of 71% only or the pure acid in a yield of 56% while another aromatic aldehyde, i.e. 4-hydroxy-3-methoxy-benzaldehyde provided no 4-hydroxy-3-methoxy-benzoic acid at all.

It has also been observed, in accordance with another aspect of the present invention, that a mixture of halogen and alkali metal hydroxide i.e. an alkali metal hypohalide such as sodium hypochlorite, hypobromite or hypoiodite when it is added to an aqueous suspension of 5-nitro-2-formyl-thiophene maintained at a pH between 4.5 and 6.5 by means of acetic acid or an acetic acid/alkali metal acetate mixture, provides pure 5-nitro-2-thenoic acid in a yield of at least 75%.

This hypohalide may be prepared by adding a halogen to an aqueous alkali metal hydroxide at a temperature between −5° C. and 0° C., the said hypohalide being subsequently added to the reaction medium maintained at a temperature between room-temperature and 40° C.

The alkali metal acetate will be preferably sodium acetate and the oxidation reaction itself will take place at a temperature between room-temperature and 80° C.

Taking into account the various aspects of the invention indicated hereabove, 5-nitro-2-thenoic acid of formula I will be obtained, in accordance with the novel process, by oxidizing 5-nitro-2-formyl-thiophene of the formula:

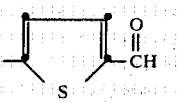

with an alkali metal hypohalide either formed extemporaneously from an alkali metal hydroxide and a halogen or formed in the reaction medium, the oxidation process consisting in introducing into an aqueous suspension of 5-nitro-2-formyl-thiophene:
either acetic acid or an acetic acid/alkali metal acetate mixture followed by a mixture comprising an alkali metal hydroxide and a halogen,
or a halogen and then an aqueous solution of alkali metal hydroxide,
or an alkali metal carbonate, an alkali metal bicarbonate or an alkali metal acetate/acetic acid mixture and then a halogen.
so that the oxidation reaction takes place at a pH between 4.5 and 11.

The halogen will be chlorine, bromine or iodine with, however, a preference for bromine.

The alkali metal will be, for instance, sodium while the oxidation reaction itself will be carried out at a temperature between room-temperature and 80° C.

From the overall results indicated above, it is evident that the process of the invention offers an undoubted advantage over the processes suggested by the prior art. In fact, the three procedures for using the reagents which, taken together, constitute the process of the invention appear to be equal to each other with respect to the yield in 5-nitro-2-thenoic acid. This is certainly not the case when 4-nitro-2-formyl-thiophene or -furan is used to obtain the corresponding acids.

Furthermore, the process of the invention has proved to be superior to the known processes used for preparing 5-nitro-2-thenoic acid.

The process of the invention is, in fact, perfectly adapted for use, on the industrial scale since it complies with the criteria listed above namely:
simplicity as regards procedure
use of crude 5-nitro-2-formyl-thiophene without undue manipulation
high yields which are more than 2.5 times the yield provided by the process described in Chemical Abstracts 47, 2166 G.
low production cost.

The following non-limitative Examples illustrate the process of the invention:

EXAMPLE 1

Preparation of 5-nitro-2-thenoic acid through oxidation by means of hypohalides formed in the reaction medium I. Oxidation in the presence of sodium acetate/acetic acid Into a 250-ml flask equipped with a central stirrer, a thermometer and a condenser, and containing 15.7 g (0.1 mol) of 5-nitro-2-formyl-thiophene, were introduced 16.4 g (0.2 mol) of sodium acetate, 16 ml of acetic acid and 100 ml of distilled water. The suspension was maintained under vigorous stirring and heated to about 40° C. Through a dropping-funnel, 16 g (0.1 mol) of bromine were then added in 15 to 20 minutes. At the end of this period, the temperature was 70° C. The mixture was allowed to react for one hour at 80° C., was poured into iced water containing hydrochloric acid and then extracted with ether. During the oxidation reaction, the pH of the reaction medium remained at 4.6.

The ethereal phase was dried on sodium sulphate and evaporated to dryness by means of a rotatory evaporator. The crude product was recrystallised from a 70/30 heptane/1,2-dichloro-ethane mixture and then brought to 0° C.

In this manner, 17 g of crude 5-nitro-2-thenoic acid were obtained, which represents a yield of 98.5% in crude product.

Yield in pure product: 14 g or 81%. M.P. of the pure product: 161° C.

II. Oxidation in the presence of sodium carbonate or bicarbonate

Into a 250-ml flask fitted with a central stirrer, a thermometer and a condenser and containing 15.7 g (0.1 mol) of 5-nitro-2-formyl-thiophene, were introduced 100 ml of distilled water and either 33.6 g (0.4 mol) of sodium bicarbonate or 21.2 g (0.2 mol) of sodium carbonate. At room-temperature, 20.8 g (1.3 mol) of bromine were then added in 10 to 15 minutes. The temperature rose spontaneously to 35°-40° C. The reaction of the bromine was immediate and gave off carbonic anhydride. The temperature was increased to 80° C. until after 30 to 35 minutes, the reaction mixture became homogeneous. The medium was cooled to 40° C. and then 37%-hydrochloric acid was poured in, drop-by-drop, to regenerate the thenoic acid formed. The ethereal phase was dried on sodium sulphate and heated to dryness by means of a rotatory evaporator. The crude solid so obtained was recrystallised from a 70/30 heptane/1,2-dichloro-ethane mixture and then brought to 0° C.

In this manner, 17 g of 5-nitro-2-thenoic acid were obtained using either sodium bicarbonate or sodium carbonate.

Yield in crude product: 98.2%

Yield in pure product: 14 g or 81%.

The use of 0.4 mol of sodium bicarbonate maintained the pH of the medium between 8 and 7.3 during the reaction while the use of 0.2 mol of sodium carbonate maintained the pH between 11 and 8.6.

III. Oxidation in the presence of sodium hydroxide

Into a 250-ml flask equipped with a central stirrer, a thermometer, a condenser and a dropping-funnel, and containing 15.7 g (0.1 mol) of 5-nitro-2-formyl-thiophene, were introduced 100 ml of distilled water and then, in one operation, 16 g (0.1 mol) of bromine.

As soon as this operation was over, a solution of 8 g of sodium hydroxide in 30 ml of water was added.

During the operation of adding the sodium hydroxide solution, the temperature of the reaction medium rose to 40° C. and the colouring provoked by the bromine disappeared. The medium was then allowed to stand for one hour at 80° C. In the course of the oxidation reaction, the pH varied from 7 to 9.5. The mixture was poured into water containing hydrochloric acid and then the thenoic acid so formed was extracted with ether. The etheral phase was dried on sodium sulphate and heated to dryness in a rotatory evaporator. The crude solid so obtained was recrystallised from a 70/30 heptane/1,2-dichloro-ethane mixture and brought to 0° C.

In this manner, 17 g of crude 5-nitro-2-thenoic acid were obtained, which represents a yield of 98.2%.

Yield in pure product: 14 g or 81%.

EXAMPLE 2

Preparation of 5-nitro-2-thenoic acid through oxidation by means of previously prepared hypohalides (a) Sodium hypobromite Into a 250-ml flask fitted with a central stirrer, a thermometer and a condenser, were introduced 100 ml of water and 10.4 g (0.26 mol) of sodium hydroxide. As soon as dissolution was terminated, the medium was cooled and maintained between −5° C. and 0° C. Then, 20.8 g (0.13 mol) of bromine were added in 20 minutes and the reaction medium was transferred to a dropping-funnel.

(b) Oxidation

Into a 250-ml flask equipped with a central stirrer, a thermometer, a condenser and a dropping-funnel, and containing 15.7 g (0.1 mol) of 5-nitro-2-formyl-thiophene, were introduced 60 ml of water and either 16 ml of acetic acid or 16 ml of acetic acid and 16.4 g of sodium acetate. The suspension was stirred and the sodium hypobromite solution previously prepared was added in 10 minutes. Just after the first drops of hypobromite had been introduced, the reaction medium turned red, which proved the formation of bromine vapours. This coloration remained throughout the oxidation reaction. When the operation of addition was over, the mixture was heated to and maintained at 80° C. for 2 hours until it became homogeneous. During the oxidation reaction, the pH of the reaction medium remained at 5.1. The mixture was then poured into water containing hydrochloric acid and extracted with ether. The etheral phase was dried on sodium sulphate and heated to dryness in a rotatory evaporator. The crude solid so obtained was recrystallised from a 70/30 heptane/1,2-dichloro-ethane mixture and brought to 0° C.

In this manner, 16 g of crude 5-nitro-2-thenoic acid were obtained, in the presence of acetic acid alone, which represents a yield of 92%.

Yield in pure product: 13 g or 75%

Starting from 0.5 mol of sodium hypobromite and 0.1 mol of 5-nitro-2-formyl-thiophene and in the presence of acetic acid/sodium acetate as mentioned above, 16 g of crude 5-nitro-2-thenoic acid were obtained, which represents a yield of 92%.

Yield in pure product: 13 g or 75%.

pH of the reaction medium during the oxidation reaction: 5.5

What we claim is:

1. Process for preparing 5-nitro-2-thenoic acid of the formula:

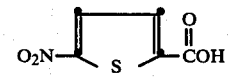

by reacting 5-nitro-2-formyl-thiophene of the formula:

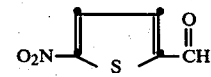

with an alkali metal hypohalide formed from alkali metal hydroxide and a halogen or formed in the reaction medium, wherein the following is introduced into an aqueous suspension of 5-nitro-2-formyl-thiophene:

either acetic acid or an acetic acid/alkali metal acetate mixture, followed by a mixture comprising an alkali metal hydroxide and a halogen, so that the oxidation reaction takes place at a pH between 4.5 and 6.5 or an alkali metal carbonate, an alkali metal bicarbonate or an alkali metal acetate/acetic acid mixture and then a halogen, so that the oxidation reaction takes place at a pH between 4.5 and 11.

2. Process according to claim 1 wherein the alkali metal is sodium.

3. Process according to claim 1 wherein the halogen is bromine.

4. Process according to claim 1 wherein the oxidation reaction takes place at a temperature between room-temperature and 80° C.

* * * * *